United States Patent [19]

Nagato et al.

[11] Patent Number: 5,024,692
[45] Date of Patent: Jun. 18, 1991

[54] HERBICIDAL COMPOSITION AND HERBICIDAL METHOD

[75] Inventors: Shoin Nagato, Tokyo; Ryusuke Taguchi, Yokohama; Kenji Hirai, Sagamihara; Hiroaki Hirose; Masahiro Yokota, both of Ichihara, all of Japan

[73] Assignees: Kaken Pharmaceutical Co., Ltd.; Sagami Chemical Research Center, both of Tokyo; Chisso Corporation, Osaka, all of Japan

[21] Appl. No.: 376,570

[22] Filed: Jul. 7, 1989

[30] Foreign Application Priority Data

Jul. 14, 1988 [JP] Japan ................................. 63-173838

[51] Int. Cl.$^5$ ............................................. A01N 57/10
[52] U.S. Cl. ............................................. 71/86; 71/88
[58] Field of Search ....................................... 71/86, 88

[56] References Cited

U.S. PATENT DOCUMENTS 3,799,758  3/1974  Franz ....................................... 71/86

FOREIGN PATENT DOCUMENTS 0241559  12/1987  European Pat. Off. .

Primary Examiner—Glennon H. Hollrah
Assistant Examiner—John D. Pak
Attorney, Agent, or Firm—Oblon, Spivak, McClelland, Maier & Neustadt

[57] ABSTRACT

A herbicidal composition comprising at least one oxazolidinedione derivative expressed by the following formula:

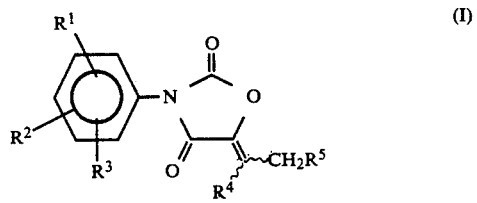

(wherein $R^1$, $R^2$ and $R^3$ independently denote hydrogen atoms, halogen atoms, nitro groups, alkyl groups, alkoxy groups, alkenyloxy groups, alkynyloxy groups or cycloalkyloxy groups; $R^4$ and $R^5$ independently denote hydrogen atoms, alkyl groups or aryl groups or may be combined with each other to form a polymethylene chain; and said alkyl groups, alkoxy groups, alkenyloxy groups, alkynyloxy groups, cycloalkyloxy groups and aryl groups may be substituted); and at least one organic phosphorus herbicide, as active ingredients.

8 Claims, No Drawings

HERBICIDAL COMPOSITION AND HERBICIDAL METHOD

The present invention relates to a herbicidal composition and a herbicidal method. More particularly, it relates to a herbicidal composition comprising at least one oxazolidinedione derivative of the formula (I) as defined hereinafter and at least one organic phosphorus herbicide, as active ingredients, and a herbicidal method by means of such a composition.

Heretofore, a number of herbicides are practically used for controlling weeds in agricultural or non-agricultural fields. However, it is still desired to develop a herbicide having high herbicidal effects and a wide herbicidal spectrum, since the weeds to be controlled include various types and their germination extends over a long period of time.

The present inventors have found that a herbicidal composition comprising at least one oxazolidinedione derivative of the formula (I) and at least one organic phosphorus herbicide, as active ingredients, is capable of quickly controlling various weeds in agricultural or non-agricultural fields, and yet it provides satisfactory effects at a dose substantially lower than the case where the active ingredients are used independently. The present invention has been accomplished on the basis of this discovery.

The present invention provides a herbicidal composition comprising at least one oxazolidinedione derivative expressed by the following formula:

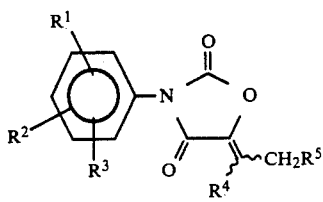

(wherein $R^1$, $R^2$ and $R^3$ independently denote hydrogen atoms, halogen atoms, nitro groups, alkyl groups, alkoxy groups, alkenyloxy groups, alkynyloxy groups or cycloalkyloxy groups; $R^4$ and $R^5$ independently denote hydrogen atoms, alkyl groups or aryl groups or may be combined with each other to form a polymethylene chain; and said alkyl groups, alkoxy groups, alkenyloxy groups, alkynyloxy groups, cycloalkyloxy groups and aryl groups may be substituted); and at least one organic phosphorus herbicide, as active ingredients.

The present invention also provides a herbicidal method which comprises applying to a locus to be protected at least one oxazolidinedione derivative of the formula (I) and at least one organic phosphorus herbicide, in combination.

With the composition of the present invention, it is now possible to control annual and perennial weeds in agricultural or non-agricultural fields.

Now, the present invention will be described in detail with reference to the preferred embodiments.

In the formula (I) $R^1$, $R^2$ and $R^3$ independently denote hydrogen atoms; nitro groups; halogen atoms such as fluorine, chlorine, bromine and iodine atoms; straight or branched chain alkyl groups having 1 to 8 carbon atoms, preferably 1 to 5 carbon atoms, such as methyl, ethyl, n-propyl, isopropyl, n-butyl, n-pentyl, n-hexyl, n-heptyl, and n-octyl groups which may be substituted by one or more halogen atoms; alkoxy groups having 1 to 18 carbon atoms, preferably 1 to 8 carbon atoms, such as methoxy, ethoxy, n-propoxy, isopropoxy, n-butoxy, t-butoxy groups which may be substituted by one or more alkoxycarbonyl groups (2 to 18 carbon atoms) or halogen atoms; cycloalkoxy groups having 3 to 12 carbon atoms, preferably 3 to 8 carbon atoms, such as cyclohexyloxy, cyclopentyloxy, and cyclopropyloxy groups which may be substituted by one or more lower alkyl groups (1 to 5 carbon atoms) or halogen atoms; straight or branched chain alkenyloxy groups having 2 to 12 carbon atoms, preferably 2 to 8 carbon atoms, such as allyloxy, methallyloxy, propenyloxy, butenyloxy, pentenyloxy and hexenyloxy groups which may be substituted by one or more halogen atoms; or straight or branched chain alkynyloxy groups having 2 to 12 carbon atoms, preferably 2 to 8 carbon atoms, such as propargyloxy, 1-methylpropargyloxy, 1,1-dimethylpropargyloxy, 2-butynyloxy, 3-butynyloxy, 2-pentynyloxy, 3-pentynyloxy groups which may be substituted by one or more halogen atoms; and $R^4$ and $R^5$ independently denote hydrogen atoms; straight or branched chain alkyl groups having 1 to 18 carbon atoms, preferably 1 to 8 carbon atoms, such as methyl, ethyl, n-propyl, isopropyl, n-butyl, isobutyl, n-hexyl, and n-octyl groups which may be substituted by one or more halogen atoms; aryl groups having 6 to 10 carbon atoms such as phenyl, p-chlorophenyl, p fluorophenyl, m, p-dimethoxyphenyl, and p-methylphenyl groups which may be substituted by halogen atoms or lower alkyl groups having 1 to 3 carbon atoms; or $R^4$ and $R^5$ may be combined with each other to form a straight or branched chain polymethylene group having 3 to 10 carbon atoms.

Typical examples of compounds expressed by the formula (I) are shown in Table 1. Particularly preferred are the following compounds:

3-{2'-fluoro-4'-chloro-5'-(1"-methylpropargyloxy)-phenyl}-5-isopropylidene-1,3-oxazolidine-2,4-dione (hereinafter referred to simply as OZ), 3-(4'-chlorophenyl)-5-(sec butylidene)-1,3-oxazolidine-2,4-dione, 3-(2'-fluoro-4'-chloro-5'-isopropoxyphenyl)-5-isopropylidene-1,3-oxazolidine-2,4-dione, 3(2'-fluoro-4'-bromo-5'-propargyloxyphenyl)-5-isopropylidene-1,3-oxazolidine-2,4-dione, 3-(2'-fluoro-4'-chloro-5'-isopropoxyphenyl)-5-isopropylidene-1,3 oxazolidine-2,4-dione, 3-(2'-fluoro-4'-chloro-5'-propargyloxyphenyl)-5-isopropylidene-1,3-oxazolidine-2,4-dione, 3-(2'-fluoro-4'-bromo-5'-propargyloxyphenyl) 5-(sec-butylidene)-1,3-oxazolidine-2,4-dione, 3-{2',4'-dichloro-5'-(1"-ethoxycarbonylethyl)oxyphenyl}-5-(sec butylidene)-1,3-oxazolidine-2,4-dione, 3-(2'-fluoro-4'-chloro-5'-methoxyphenyl)-5-isopropylidene-1,3-oxazolidine-2,4-dione, 3-(2'-fluoro-4'-chloro-5'-propargyloxyphenyl)-5-(sec-butylidene)-1,3-oxazolidine-2,4-dione, 3-(2'-fluoro-4'-chloro-5'-cyclopentyloxyphenyl)-5isopropylidene 1,3-oxazolidine-2,4-dione, 3-{2'-fluoro 4'-chloro-5'-(2"-chloroallyl)oxyphenyl}-5-isopropylidene-1,3-oxazolidine 2,4-dione, 3-{2'-fluoro-4'-chloro-5'-(1"-ethoxycarbonylethyl)-oxyphenyl}-5-isopropylidene-1,3-oxazolidine-2,4-dione, 3-(2'-fluoro-4'-bromo-5'-allyloxyphenyl)-5-isobutylidene 1,3-oxazolidine-2,4-dione, and 3(2'-fluoro-4'-chloro-5'-allyloxyphenyl)-5-isopropylidene-1,3-oxazolidine-2,4-dione.

TABLE 1

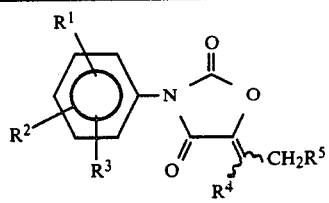

| Compound No. | R¹ | R² | R³ | R⁴ | R⁵ |
|---|---|---|---|---|---|
| 1 | H | H | H | $CH_3$ | H |
| 2 | H | H | H | $C_2H_5$ | $CH_3$ |
| 3 | H | H | H | $CH_3$ | p-Cl—$C_6H_4$ |
| 4 | 4-Cl | H | H | $CH_3$ | H |
| 5 | 4-F | H | H | $CH_3$ | H |
| 6 | 2-F | H | H | $CH_3$ | H |
| 7 | 4-Cl | H | H | $CH_3$ | $CH_3$ |
| 8 | 4-Br | H | H | $CH_3$ | $CH_3$ |
| 9 | 4-F | H | H | $CH_3$ | $CH_3$ |
| 10 | 4-Cl | H | H | $CH_3$ | n-Pr |
| 11 | 4-Cl | H | H | $CH_3$ | n-$C_5H_{11}$ |
| 12 | 4-Cl | H | H | $C_2H_5$ | $CH_3$ |
| 13 | 4-Cl | H | H | $-(CH_2)_4-$ | |
| 14 | 3-Cl | 4-Cl | H | $CH_3$ | H |
| 15 | 3-Cl | 5-Cl | H | $CH_3$ | H |
| 16 | 2-Cl | 4-Cl | H | $CH_3$ | H |
| 17 | 2-Cl | 4-Cl | H | $C_2H_5$ | $CH_3$ |
| 18 | 3-Cl | 5-Cl | H | $C_2H_5$ | $CH_3$ |
| 19 | 3-Cl | 5-Cl | H | $-(CH_2)_3-$ | |
| 20 | 3-Cl | 4-Cl | H | $C_6H_5$ | H |
| 21 | 3-Cl | 4-Cl | H | p-Cl—$C_6H_4$ | H |
| 22 | 3-Cl | 5-Cl | H | p-Cl—$C_6H_4$ | H |
| 23 | 2-F | 4-F | H | $CH_3$ | H |
| 32 | 2-F | 4-Cl | 5-HC≡$CCH_2O$ | $CH_3$ | H |
| 33 | 2-F | 4-Cl | 5-HC≡$CCH_2O$ | $CH_3$ | $CH_3$ |
| 34 | 2-F | 4-Br | 5-HC≡$CCH_2O$ | $CH_3$ | H |
| 35 | 2-F | 4-Br | 5-HC≡$CCH_2O$ | $CH_3$ | $CH_3$ |
| 36 | 2-F | 4-Cl | 5-HC≡$CCH_2O$— with $CH_3$ substituent | $CH_3$ | H |
| 37 | 2-F | 4-Cl | 5-$H_3CC$≡$CCH_2CH_2O$ | $CH_3$ | H |
| 38 | 2-Cl | 4-Cl | 5-$H_3CC$≡$CCH_2CH_2O$ | $CH_3$ | H |
| 39 | 2-F | 4-Cl | 5-$H_2C$=$CHCH_2O$ | $CH_3$ | H |
| 40 | 2-F | 4-Br | 5-$H_2C$=$CHCH_2O$ | $CH_3$ | $CH_3$ |
| 41 | 2-F | 4-Cl | 5-$H_2C$=$C(CH_3)CH_2O$ | $CH_3$ | H |
| 42 | 2-Cl | 4-Cl | 5-$H_2C$=$C(CH_3)CH_2O$ | $CH_3$ | H |
| 43 | 2-F | 4-Br | 5-HC(Cl)=$CHCH_2O$ | $CH_3$ | $CH_3$ |
| 44 | 2-F | 4-Cl | 5-$H_2C$=$C(Cl)CH_2O$ | $CH_3$ | H |
| 45 | 2-F | 4-Cl | 5-$H_3CCH$=$C(Br)CH_2O$ | $CH_3$ | H |
| 46 | 2-F | 4-Cl | 5-$CH_3CH_2OC(=O)CH(CH_3)O$ | $CH_3$ | H |
| 47 | 2-F | 4-Cl | 5-$CH_3CH_2OC(=O)CH(CH_3)O$ | $CH_3$ | $CH_3$ |
| 48 | 2-Cl | 4-Cl | 5-$CH_3CH_2OC(=O)CH(CH_3)O$ | $CH_3$ | H |
| 49 | 2-Cl | 4-Cl | 5-$CH_3CH_2OC(=O)CH(CH_3)O$ | $CH_3$ | $CH_3$ |
| 50 | 2-Cl | 4-Cl | 5-(2-ethylhexyl)$OC(=O)CH_2O$ | $CH_3$ | H |

TABLE 1-continued

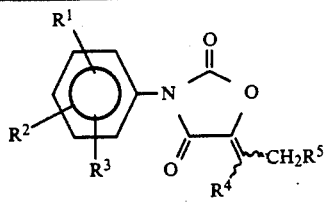

| Compound No. | R¹ | R² | R³ | R⁴ | R⁵ |
|---|---|---|---|---|---|
| 51 | 2-Cl | 4-Cl | 5-CH₃O | CH₃ | CH₃ |
| 52 | 2-F | 4-Cl | 5-CH₃O | CH₃ | H |
| 53 | 2-F | 4-Cl | 5-(CH₃)₂CHO | CH₃ | CH₃ |
| 54 | 2-F | 4-Br | 5-(CH₃)₂CHO | CH₃ | CH₃ |
| 55 | 2-F | 4-Cl | 5-cyclo-C₅H₉O | CH₃ | H |
| 56 | 2-F | 4-Cl | 5-cyclo-C₆H₁₁O | CH₃ | H |

These compounds have strong herbicidal effects against aerial parts of annual and perennial weeds. They are particularly effective against weeds in an initial growing stage with a height of about 10 cm and capable of quickly killing new buds or foliages of weeds. However, their effects do not extend to roots of weeds, whereby perennial weeds or some annual weeds will recover. Further, weeds in an advanced growth stage will be affected only partially at their foliages, and they will recover and will grow thick again.

On the other hand, the organic phosphorus herbicide used in the present invention is usually a herbicidally effective substance having phosphorus in the chemical structure, such as N-(phosphonomethyl)glycine (hereinafter referred to simply as PG) or its salt, DL-homoalanin-4-yl (methyl)phosphinic acid (hereinafter referred to simply as PA) or its salt, or L-2-amino-4-{(hydroxy)(methyl)phosphinoyl]butyryl-L-alanyl-L-alanine (hereinafter referred to simply as PAA) or its salt, S-(2-methylpiperidin 1-ylcarbonylmethyl) O,O di-propylphosphorodithioate, O methyl O-(2 nitro-4-methylphenyl) N isopropylphosphoroamidethioate, O-ethyl O-(3-methyl 6 nitrophenyl) sec butylphosphoroamide thioate, O,O-diisopropyl S-(2-phenylsulfonylaminoethyl)-phosphorodithioate, or ethyl ammonium carbamoyl phosphonate. Particularly preferred is an amino acid compound containing phosphorus, such as N-(phosphonomethyl)glycine or its salt, DL-homoalanin-4-yl (methyl)phosphinic acid or its salt, or L-2-amino-4-{(hydroxy)(methyl)phosphinoyl}butyryl-L-alanyl-L-alanine or its salt. As such salt, a sodium salt, a potassium salt, a calcium salt, an ammonium salt, a trimethylsulfonium salt, an isopropylamine salt or a trimethylsulfoxonium salt, is preferred.

Some of such organic phosphorus herbicides are already commercially available. However, they require a relatively long period of at least one week to kill most of weeds even at a usual dose of at least about 5 g/are. At a low dose, they do not provide adequate effects not only against perennial weeds but also against annual weeds, whereby weeds will regain growth and will grow thick.

The present inventors have found that by combined use of at least one oxazolidinedione derivative of the formula (I) and at least one organic phosphorus herbicide having the above drawbacks in their single use, it is possible to complement the respective drawbacks, to increase the useful period and to kill almost all the weeds in agricultural or non-agricultural fields quickly and at a low dose in a single application.

The present invention has been accomplished on the basis of this discovery.

To practice the present invention, the above-mentioned two active ingredients are simultaneously or separately mixed with an adjuvant such as a solid carrier, a liquid diluent, a surfactant, an extender or the like and formulated into a wettable powder, a suspension or an emulsifiable concentrate. When the respective active ingredients are formulated independently, they are mixed or combined for application. In the case of a formulation containing the two active ingredients in admixture, the formulation is diluted with water and applied to weeds. The doses of the respective active ingredients in the combined use vary depending upon the types of the compounds and salts, the types and the growing stages of weeds, the application method, etc. However, the dose of the oxazolidinedione derivative of the formula (I) is usually from 0.5 to 60 g/are, preferably from 1 to 30 g/are, and the dose of the organic phosphorus herbicide is usually from 2 to 100 g/are, preferably from 4 to 50 g/are.

The solid carrier useful for formulation includes, for example, kaolin, bentonite, clay, talc and zeolite. The liquid carrier includes, for example, water, xylene, methylnaphthalene, ethanol, isopropanol, ethylene glycol, acetone, soybean oil and cotton oil. The surfactant includes, for example, a polyoxyethylenealkyl ether and a polyoxyethylene fatty acid ester.

Now, Formulation Examples will be given, in which "parts" means "parts by weight".

FORMULATION EXAMPLE 1 OZ wettable powder

Fifty parts of OZ, 25 parts of diatomaceous earth, 22 parts of clay and 3 parts of Runox R100C (manufactured by Toho Chemical Co., Ltd.) were uniformly mixed and ground to form a wettable powder.

FORMULATION EXAMPLE 2 OZ emulsifiable concentrate

Twenty parts of OZ, 75 parts of xylene and 5 parts of Sorpol 900A (manufactured by Toho Chemical Co., Ltd.) were uniformly dissolved to form an emulsifiable concentrate.

FORMULATION EXAMPLE 3 Wettable powder

Ten parts of OZ, 40 parts of PG isopropylamine salt, 5 parts of calcium lignin sulfonate and 45 parts of water-containing silicon oxide were uniformly mixed and ground to form a wettable powder.

FORMULATION EXAMPLE 4 Wettable powder

Twelve parts of OZ, 48 parts of PAA sodium salt, 35 parts of diatomaceous earth and 5 parts of a polyoxyethylene alkyl phenyl ether were uniformly mixed and ground to form a wettable powder.

FORMULATION EXAMPLE 5 Suspension

Five parts of OZ, 20 parts of PA ammonium salt, 5 parts of sorbitan monooleate, 5 parts of carboxymethyl cellulose and 65 parts of water were mixed and homogenized to form a suspension.

Now, the herbicidal effects of the present invention will be described in detail with reference to Test Examples.

TEST EXAMPLE 1 Test for synergistic effects by the combined use

A Wagner pot having an area of 1/5,000 are was filled with upland soil, and about 20 seeds of *Echinochloa frumentacea* (edible barnyard grass) were sown and cultured for 25 days. Then, the OZ emulsifiable concentrate of Formulation Example 2 and an organic phosphorus herbicide were mixed to present the predetermined doses, then diluted with water corresponding to 10 l/are and sprayed to the foliage of *Echinochloa frumentacea* (edible barnyard grass) by means of a sprayer. At the time of the application, the plant was in a 3 to 4 leaf stage, and the height was from 20 to 30 cm.

On the 20th day after the application, the herbicidal effects were examined, and the results are shown in Table 2.

The herbicidal effects are represented by the growth control rate C(%) calculated by the following equation from the weight of the aerial part of the plant remained alive at the time of the examination.

$$C(\%) = \left[1 - \frac{\text{Weight of alive aerial part in treated area}}{\text{Weight of alive aerial part in non-treated area}}\right] \times 100$$

In Table 2, the value E is an expected value calculated by a Colby equation. The Colby equation is used to determine a synergistic effect and is represented as follows:

$$E = \alpha + [\beta(100 - \alpha)/100]$$

where $\alpha$ is the growth control rate (%) of herbicide A by a a gram treatment, $\beta$ is the growth control rate (%) of herbicide B by a b gram treatment, and E is the expected value (%) of the growth control rate by the combined use of the two herbicides. When the measured value is C%, the two herbicides are regarded to have a synergistic effect if C>E.

TABLE 2

| Tested herbicides | | Doses of active ingredients (g/are) | | Herbicidal effects (%) | |
|---|---|---|---|---|---|
| Oxazolidinedione | Organic phosphorus herbicide | Oxazolidinedione | Organic phosphorus herbicide | C | E |
| OZ | — | 0.5 | — | 40 | — |
| | | 1 | — | 50 | — |
| | | 2 | — | 70 | — |
| | | 5 | — | 80 | — |

TABLE 2-continued

| Tested herbicides | | Doses of active ingredients (g/are) | | Herbicidal effects (%) | |
|---|---|---|---|---|---|
| Oxazolidinedione | Organic phosphorus herbicide | Oxazolidinedione | Organic phosphorus herbicide | C | E |
| | | 10 | — | 100 | — |
| — | PG isopropylamine salt | — | 2.5 | 10 | — |
| | | — | 5 | 30 | — |
| | | — | 10 | 65 | — |
| | | — | 20 | 100 | — |
| — | PA ammonium salt | — | 2.5 | 40 | — |
| | | — | 5 | 60 | — |
| | | — | 10 | 75 | — |
| | | — | 20 | 100 | — |
| — | PAA sodium salt | — | 2.5 | 25 | — |
| | | — | 5 | 40 | — |
| | | — | 10 | 70 | — |
| | | — | 20 | 100 | — |
| OZ | PG isopropylamine salt | 0.5 | 2.5 | 75 | 46 |
| | | 0.5 | 5 | 90 | 58 |
| | | 0.5 | 10 | 100 | 79 |
| | | 1 | 2.5 | 95 | 55 |
| | | 1 | 5 | 100 | 65 |
| | | 1 | 10 | 100 | 82.5 |
| | | 2 | 2.5 | 100 | 73 |
| | | 2 | 5 | 100 | 79 |
| | | 2 | 10 | 100 | 89.5 |
| | | 5 | 2.5 | 100 | 82 |
| | | 5 | 5 | 100 | 86 |
| | | 5 | 10 | 100 | 93 |
| OZ | PA ammonium salt | 0.5 | 2.5 | 90 | 64 |
| | | 0.5 | 5 | 100 | 76 |
| | | 0.5 | 10 | 100 | 85 |
| | | 1 | 2.5 | 95 | 70 |
| | | 1 | 5 | 100 | 80 |
| | | 1 | 10 | 100 | 87.5 |
| | | 2 | 2.5 | 100 | 82 |
| | | 2 | 5 | 100 | 88 |
| | | 2 | 10 | 100 | 92.5 |
| | | 5 | 2.5 | 100 | 88 |
| | | 5 | 5 | 100 | 92 |
| | | 5 | 10 | 100 | 95 |
| OZ | PAA sodium salt | 0.5 | 2.5 | 85 | 55 |
| | | 0.5 | 5 | 95 | 64 |
| | | 0.5 | 10 | 100 | 82 |
| | | 1 | 2.5 | 95 | 62.5 |
| | | 1 | 5 | 100 | 70 |
| | | 1 | 10 | 100 | 85 |
| | | 2 | 2.5 | 100 | 77.5 |
| | | 2 | 5 | 100 | 82 |
| | | 2 | 10 | 100 | 91 |
| | | 5 | 2.5 | 100 | 85 |
| | | 5 | 5 | 100 | 88 |
| | | 5 | 10 | 100 | 94 |

TEST EXAMPLE 2 Herbicidal effects with time by the combined use against Cyperus rotundus (purple nutsedge)

A seedling case (5.5×15 cm, depth: 11 cm) was filled with upland soil, and three tubers of *Cyperus rotundus* (purple nutsedge) were transplanted and cultured for 30 days. Then, the OZ wettable powder of Formulation Example 1 and an organic phosphorus herbicide were mixed to present the predetermined doses, dilued with water corresponding to 10 l/are and sprayed to the foliage of *Cyperus rotundus* (purple nutsedge) by means of a sprayer. The spraying was conducted within a cylindrical frame having an area of 1/2,000 are. At the time of the application, the plant was in a 5 to 7 leaf stage, and the height was from 20 to 40 cm. On the 4th, 7th, 14th and 24th day after the application, leaf dying was examined. The results are shown in Table 3. The herbicidal effects were evaluated generally in accordance with the following standards.

Herbicidal indices

0: same as non-treatment (0-5% leaf dying)
1: 6-20% leaf dying.
2: 21-40% leaf dying
3: 41-70% leaf dying
4: 71-95% leaf dying
5: at least 96% leaf dying

TABLE 3

| Tested herbicides | | Doses of active ingredients (g/are) | | Herbicidal effects (%) | | | |
|---|---|---|---|---|---|---|---|
| OXAZO | Organic phosphorus herbicide | OXAZO | Organic phosphorus herbicide | 4th | 7th | 14th | 24th |
| OZ | — | 3 | — | 3 | 5 | 3 | 2 |
|  |  | 10 | — | 4 | 5 | 4 | 3 |
| — | PG iso-propyl-amine salt | — | 10 | 0 | 1 | 2 | 3 |
|  |  | — | 30 | 0 | 2 | 4 | 5 |
| — | PA am-monium salt | — | 10 | 1 | 2 | 3 | 4 |
|  |  | — | 30 | 1 | 4 | 5 | 5 |
| — | PAA sodium salt | — | 10 | 0 | 2 | 3 | 3 |
|  |  | — | 30 | 1 | 3 | 4 | 5 |
| OZ | PG iso-propyl-amine salt | 3 | 10 | 3 | 4 | 5 | 5 |
| OZ | PA am-monium salt | 3 | 10 | 4 | 4 | 5 | 5 |
| OZ | PAA sodium salt | 3 | 10 | 4 | 5 | 5 | 5 |

OXAZO: Oxazolidinedione

TEST EXAMPLE 3 Test for foliar treatment spectrum

A planter (12×25 cm, depth: 11 cm) was filled with upland soil, and seeds of *Digitaria adscendens* (crabgrass), *Setaria viridis* (green foxtail), *Phleum pratense* L. (timothy), *Lolium perenne* L. (perennial ryegrass), *Avena sativa* L. (oat), *Chenopodium album* L. (common lambsquarters), *Polygonum blumei* (persicaria blumei gross), *Amaranthus lividus* L. (livid amaranth), *Lamium amplexicaule* L. (henbit) and *Commelina communis* L. (dayflower) were sown, and rhizomes or tubers of *Artemisia princeps* (mugwort) and *Cyperus rotundus* (purple nutsedge) were transplanted. They were cultured for 30 days. Then, the herbicides were mixed to present the predetermined doses, then diluted with water corresponding to 10 l/are and sprayed to the foliages of the plants by means of a sprayer. At the time of the spray treatment, the plants were in a 3 to 6 leaf stage, and the height was from 5 to 40 cm, although they varied depending upon the types of the plants. On the 20th day after the treatment, the herbicidal effects (%) were examined, whereby 100% means complete kill. The results are shown in Table 4.

TABLE 4

| Tested herbicides | | Doses of active ingredients (g/are) | | Herbicidal effects (%) | | | | | | | | | | | |
|---|---|---|---|---|---|---|---|---|---|---|---|---|---|---|---|
| OXAZO | Organic phosphorus herbicide | OXAZO | Organic phosphorus herbicide | DI | SE | PH | LO | AV | CH | PO | AM | LA | CO | AR | CY |
| OZ | — | 2.5 | — | 45 | 40 | 60 | 45 | 50 | 70 | 85 | 80 | 65 | 35 | 55 | 30 |
| — | PG isopropylamine salt | — | 10 | 60 | 65 | 65 | 50 | 65 | 70 | 65 | 75 | 70 | 55 | 65 | 50 |
| — | PA ammonium salt | — | 10 | 75 | 75 | 65 | 60 | 80 | 95 | 80 | 80 | 85 | 60 | 75 | 75 |
| — | PAA sodium salt | — | 10 | 65 | 70 | 60 | 55 | 70 | 80 | 75 | 80 | 80 | 60 | 70 | 60 |
| OZ | PG isopropylamine salt | 2.5 | 10 | 100 | 100 | 100 | 100 | 100 | 100 | 100 | 100 | 100 | 100 | 100 | 100 |
| OZ | PA ammonium salt | 2.5 | 10 | 100 | 100 | 100 | 100 | 100 | 100 | 100 | 100 | 100 | 100 | 100 | 100 |
| OZ | PAA sodium salt | 2.5 | 10 | 100 | 100 | 90 | 100 | 90 | 100 | 100 | 100 | 100 | 100 | 100 | 95 |

OXAZO: Oxazolidinedione
DI: *Digitaria adscendens* (crabgrass), SE: *Setaria viridis* (green foxtail), PH: *Phleum pratense* L. (timothy), LO: *Lolium perenne* L. (perennial ryegrass), AV: *Avena sative* L. (oat), CH: *Chenopodium album* L. (common lambsquarters), PO: *Polygonum blumei* (persicaria blumei gross), AM: *Amaranthus lividus* L. (livid amaranth), LA: *Lamium amplexicaule* L. (henbit), CO: *Commelina communis* L. (dayflower), AR: *Artemisia princeps* (mugwort), CY: *Cyperus rotundus* (purple nutsedge)

We claim:

1. A herbicidal composition consisting essentially of a synergistically effective amount of the combination of an oxazolidinedione having the formula:

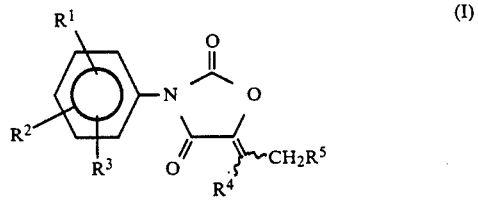

wherein $R^1$, $R^2$ and $R^3$ are, independently, halogen, lower alkenyloxy or lower alkynyloxy; $R^4$ and $R^5$ are, independently, hydrogen or lower alkyl; and a phosphorus-containing amino acid compound or its salt selected from the group consisting N-(phosphonomethyl) glycine, DL-homoalanin-4-yl-(methyl)phosphinic acid, L-2-amino-4-{(hydroxy)(methyl)-phosphinyl}butyryl-L-alanyl-L-alanine and salts thereof, wherein the ratio of said oxazolidinedione to said phosphorus-containing amino acid compound or its salt is about 1:1.125 to about 1:10.

2. The herbicidal composition according to claim 1, wherein said oxazolidinedione is selected from the group consisting of:
3-{2'-fluoro-4'-chloro-5'-(1''-methylpropargyloxy) phenyl}-5-isopropylident-1,3-oxazolidine-2,4-dione,
3-(2'-fluoro-4'-bromo-5'-propargyloxyphenyl)-5 -isopropylidene-1,3-oxazolidine-2,4-dione,
3-(2'-fluoro-4'-chloro-5'-propargyloxyphenyl)-5 -isopropylidene-1,3-oxazolidine-2,4-dione,
3-(2'-fluoro-4'-chloro-5'propargyloxyphenyl)-5 -(sec-butylidene)-1,3-oxazolidine-2,4-dione, and
3-(2'-fluoro-4'-chloro-5'-allyloxyphenyl)-5 -isopropylidene-1,3-oxazolidine-2,4-dione.

3. The herbicidal composition according to claim 2, wherein the amino acid compound is N-(phosphonomehyl)glycine or its salt, DL-homoalanin-4-yl (methyl)phosphinic acid or its salt, or L-2-amino-4-{hydroxy)(methyl)phosphinoyl}butyryl-L-alanyl-L-alanine or its salt.

4. The herbicidal composition according to claim 2, wherein the amino acid compound is N-(phosphonomethyl)glycine or its isopropylamine salt, DL-homoalanin-4-yl (methyl)phosphinic acid or its ammonium salt, or L-2-amino-4-{(hydroxy)(methyl)phosphinoyl}-butyryl-L-alanyl-L-alanine or its sodium salt.

5. The herbicidal composition according to claim 1, wherein the oxazolidinedione is 3-{2'-fluoro-4'-chloro-5'-isopropylidene-1,3-oxazolidine-2,4-dione.

6. The herbicidal composition according to claim 4, wherein the oxazolidinedione is 3-{2'-fluoro-4'-chloro-5'-(1''-methylpropargyloxy)phenyl}-5 -isopropylidene-1,3-oxazolidine-2,4-dione.

7. A herbicidal method which comprises applying to Echinochloa frumentacea plants, a synergistically effective amount of the combination of an oxazolidinedione having the formula

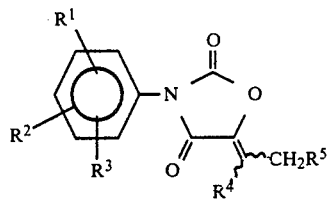

wherein $R^1$, $R^2$ and $R^3$ are, independently, halogen, lower alkenyloxy or lower alkynyloxy; $R^4$ and $R^5$ are, independently, hydrogen or lower alkyl; and a phosphorus-containing amino acid compound or its salt selected from the group consisting N-(phosphonomethyl) glycine, DL-homoalanin-4-yl -(methyl)phosphinic acid, L-2-amino-4-{(hydroxy)(methyl) -phosphinyl}butyryl-L-alanyl-L-alanine and salts thereof, wherein the ratio of said oxazolidinedione to said phosphorus-containing amino acid or its salt is about 1:1.125 to about 1:10.

8. The method according to claim 7, wherein said oxazolidinedione is selected from the group consisting of:
3-{2'-fluoro-4'-chloro-5'-(1''-methylpropargyloxy)-phenyl}-5-isopropylidene-1,3-oxazolidine-2,4-dione,
3-(2'-fluoro-4'-bromo-5'-propargyloxyphenyl)-5 -isopropylidene-1,3-oxazolidine-2,4-dione,
3-(2'-fluoro-4'-chloro-5'-propargyloxyphenyl)-5 -isopropylidene-1,3-oxazolidine-2,4-dione,
3-(2'-fluoro-4'-chloro-5'-propargyloxyphenyl)-5 -(sec-butylidene)-1,3-oxazolidine-2,4-dione, and
3-(2'-fluoro-4'-chloro-5'-allyloxyphenyl)-5 -isopropylidene-1,3-oxazolidine-2,4-dione.

* * * * *